United States Patent
Cho et al.

(10) Patent No.: US 8,557,543 B2
(45) Date of Patent: Oct. 15, 2013

(54) POLYPEPTIDES SPECIFICALLY BINDING TO VASCULAR ENDOTHELIAL GROWTH FACTOR RECEPTOR-2 AND METHODS THEREFOR

(75) Inventors: A-yeon Cho, Seongnam-si (KR); Min-kyung Kim, Seoul (KR); Brian Hosung Min, Seongnam-si (KR); Jong-sang Ryu, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 119 days.

(21) Appl. No.: 12/973,468

(22) Filed: Dec. 20, 2010

(65) Prior Publication Data

US 2011/0158994 A1    Jun. 30, 2011

(30) Foreign Application Priority Data

Dec. 22, 2009  (KR) .......................... 10-2009-0129131

(51) Int. Cl.
*C12N 15/09*  (2006.01)
*C12N 1/21*   (2006.01)
*C12N 5/10*   (2006.01)
*C07H 21/04*  (2006.01)
*C07K 14/435* (2006.01)

(52) U.S. Cl.
USPC ....... 435/69.1; 435/252.3; 435/325; 530/350; 536/23.1; 536/23.4

(58) Field of Classification Search
None
See application file for complete search history.

(56) References Cited

PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*

* cited by examiner

*Primary Examiner* — Christine J Saoud
*Assistant Examiner* — Jon M Lockard
(74) *Attorney, Agent, or Firm* — Leydig, Voit & Mayer, Ltd.

(57) ABSTRACT

A polypeptide inhibiting binding between vascular endothelial growth factor receptor-2 and a vascular endothelial growth factor, a fusion protein including the same, and a method of preparing the fusion protein are disclosed.

11 Claims, 2 Drawing Sheets

POLYPEPTIDES SPECIFICALLY BINDING TO VASCULAR ENDOTHELIAL GROWTH FACTOR RECEPTOR-2 AND METHODS THEREFOR

CROSS-REFERENCE TO RELATED APPLICATIONS

This application claims priority to Korean Patent Application No. 10-2009-0129131, filed on Dec. 22, 2009, and all the benefits accruing therefrom under 35 U.S.C. §119, the disclosure of which is incorporated herein in its entirety by reference.

BACKGROUND

1. Field

The present disclosure relates to polypeptides inhibiting binding between vascular endothelial growth factor receptor-2 and a vascular endothelial growth factor, fusion proteins including the polypeptides, and a method of preparing the fusion proteins.

2. Description of the Related Art

Angiogenesis is a process involving growth of new blood vessels from existing vessels, which plays a vital role in formation of organs, normal biological growth, and wound healing. In addition, abnormal angiogenesis is known to be an important contributor to diseases such as development and metastasis of tumor cells, age-related macular degeneration, diabetic retinopathy, psoriasis, rheumatoid arthritis, and chronic inflammation.

The development and metastasis of tumor cells depend on angiogenesis. Thus, since a hypothesis in which anti-angiogenesis therapeutic drugs would become novel anti-cancer therapeutic drugs was proposed, research into the mechanism of angiogenesis has been conducted to develop a new anti-cancer therapeutic drug. Among various angiogenesis factors, research into the function of vascular endothelial growth factor (VEGF) has been most actively conducted. When tumor tissues develop, the tumor tissues cause vessel regression and the tumor tissues are excessively grown to form a hypoxic environment therein. As a result, conditions at which angiogenesis occurs are provided within tumor tissue. Under these conditions, vascular endothelial cells increase expression of VEGF to form new vessels around tumor cells. Since the growth of the vascular endothelial cells and vascular formation are induced by expression of VEGF and reaction between VEGF and its receptor, the reactions described above are a vital process in angiogenesis. Thus, angiogenesis in tumor tissue is suppressed by inhibiting binding between the vascular endothelial growth factor receptor (VEGFR) and VEGF, and a compound that inhibits binding between VEGFR and VEGF may become an anti-cancer drug candidate or provide a target for developing anti-cancer therapies. In addition, VEGFR may emerge as a target for effective anti-cancer therapies since VEGFR is a protein, which initiates transduction of intracellular signals of vascular formation.

Although an inhibitor of VEGFR tyrosine kinase is known, in clinical trials this inhibitor was shown to be thromboembolic and severely toxic.

SUMMARY

Provided are polypeptides inhibiting binding between vascular endothelial growth factor receptor-2 and a vascular endothelial growth factor.

Provided are fusion proteins including the polypeptides inhibiting binding between vascular endothelial growth factor receptor-2 and a vascular endothelial growth factor and an antibody Fc region.

Polynucleotides encoding the fusion proteins are also provided.

Provided are recombinant vectors including the polynucleotides encoding the fusion proteins and host cells expressing the fusion proteins Provided are methods of preparing the fusion protein including a polypeptide inhibiting binding between vascular endothelial growth factor receptor-2 and a vascular endothelial growth factor and an Fc region of an antibody. In an embodiment, the method includes culturing a host cell disclosed herein under conditions that allow expression of the fusion protein, and collecting the fusion protein expressed from the culture.

Methods of treating an angiogenesis-related disease or cancer in a subject are also provided. In an embodiment, the method includes administering to a subject having an angiogenesis-related disease or cancer a therapeutically effective amount of a fusion protein disclosed here.

BRIEF DESCRIPTION OF THE DRAWINGS

These and/or other aspects of the present invention will become apparent and more readily appreciated from the following description of the embodiments, taken in conjunction with the accompanying drawings of which.

DETAILED DESCRIPTION

Reference will now be made in detail to embodiments of the invention, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

According to an embodiment of the present invention, there is provided a polypeptide that has an amino acid sequence represented by Formula I below and inhibits binding between vascular endothelial growth factor receptor-2 (VEGFR-2) and a vascular endothelial growth factor:

<Formula I>
His-Ile-$X_1$-$X_2$-Gly-Gln-Trp-Phe    (SEQ ID NO: 37)

In Formula I, $X_1$ denotes an amino acid selected from the group consisting of Asn, Cys, Gln, Gly, Ser, Thr, Try, Asp, Glu, Arg, His, and Lys, and $X_2$ denotes an amino acid selected from the group consisting of Ala, Ile, Leu, Met, Phe, Pro, Trp, Val, Asp, Glu, Arg, His, and Lys.

The polypeptide may have an amino acid sequence selected from the group consisting of SEQ ID NOS: 1 through 3.

According to an embodiment of the present invention, there is provided a polypeptide that has one amino acid sequence selected from the group consisting of SEQ ID NOS: 4 through 13 and inhibits binding between vascular endothelial growth factor receptor-2 and a vascular endothelial growth factor.

The term "vascular endothelial growth factor (VEGF)" used herein refers to a family of proteins involved in growing endothelial cells to create new blood vessels. A VEGF is secreted as a dimeric glycoprotein, and contains 8 cysteine residues. For example, the VEGF may be a protein having an amino acid sequence published as Genbank Accession No. AAL27630 or AAA35798.

The term "vascular endothelial growth factor receptor (VEGFR)" used herein refers to a type of receptor tyrosine kinase existing in cell membranes of vascular endothelial cells, which allows induction of angiogenesis by transducing signals into cells when a ligand, e.g., a vascular endothelial growth factor, binds to the VEGFR. There are three kinds of vascular endothelial growth factor receptors, such as VEGFR-1, VEGFR-2, and VEGFR-3. The VEGFR consists of 7 immunoglobulin-like domains, a single transmembrane domain, and an intracellular kinase domain. For example, the VEGFR may be a protein comprising an amino acid sequence published as GenBank Accession No. ACF47599. A polypeptide disclosed herein may specifically bind vascular endothelial growth factor receptor-2 (VEGFR-2), thereby inhibiting binding between VEGFR-2 and the vascular endothelial growth factor.

The term "specifically binding" used herein is known to one of ordinary skill in the art, and indicates that an interaction occurs between molecules of at least two polypeptides or proteins by a covalent bond or a non-covalent bond with a high affinity. For example, an antibody and an antigen specifically bind to each other to immunologically react with each other.

The term "polypeptide" used herein refers to a chain of amino acid residues linked together by peptide bonds. For example, the polypeptide may have 4-20 amino acid residues, but is not limited thereto. In some embodiments, "polypeptide" refers to inhibitor polypeptides disclosed herein which can also inhibit another polypeptide or protein.

A polypeptide may be prepared using one of various methods known in the art, such as a gene cloning method or solid-phase synthesis techniques. In addition, a polypeptide may be experimentally obtained from a commercially available polypeptide library (for example, polypeptide libraries manufactured by Dyax, bacteriophage M13-polypeptide library manufactured by New England Biolab, and the like).

In Formula I, Asn, Cys, Gln, Gly, Ser, Thr, and Try are polar amino acids with uncharged R groups, Asp, Glu, Arg, His, and Lys are amino acids with charged R groups, and Ala, Ile, Leu, Met, Phe, Pro, Trp, and Val are non-polar amino acids with R groups.

According to an embodiment of the present invention, there is provided a fusion protein including the polypeptide that has an amino acid sequence represented by Formula I and that inhibits binding between VEGFR-2 and a VEGF; and an antibody Fc region. In some embodiments, the polypeptide that has an amino acid sequence represented by Formula I may have an amino acid sequence selected from the group consisting of SEQ ID NO:1 through SEQ ID NO: 3.

According to an embodiment of the present invention, there is provided a fusion protein including a polypeptide that has an amino acid sequence selected from the group consisting of SEQ ID NOS: 4 through 13 and that inhibits binding between VEGFR-2 and a VEGF; and an antibody Fc region.

The fusion protein may further include a linker that links the polypeptide to the Fc region of the antibody.

The fusion protein may also be referred to as a peptibody. The term "peptibody" used herein refers to molecules including at least one polypeptide directly or indirectly linked to an Fc region of an antibody. The polypeptide may specifically bind a target. For example, the polypeptide in the peptibody may be a polypeptide that inhibits binding between VEGFR-2 and a VEGF.

The term, "link", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker.

The fusion protein may include a linker, for example, a peptide linker. Various known linkers in the art may be used. The linker may be a peptide linker consisting of a plurality of amino acid residues. The peptide linker may allow the polypeptide that inhibits binding between VEGFR-2 and a VEGF and the polypeptide consisting of an Fc region of an antibody to be spaced apart from each other by a sufficient distance so that each of the polypeptide domains is folded in its appropriate secondary and tertiary structures. For example, the peptide linker may include Gly, Asn and Ser residues, and may also include neutral amino acid residues, such as Thr and Ala. Amino acid sequences suitable for the peptide linker are well-known in the art. For example, the amino acid sequence may be $(Gly_4\text{-}Ser)_3$ or $Gly_4\text{-}Ser\text{-}Gly_5\text{-}Ser$. The linker may be unnecessary or may have various lengths, as long as it does not affect the biological activity of the fusion protein. The polypeptide that inhibits binding between VEGFR-2 and a VEGF and the polypeptide consisting of an Fc region of an antibody may be consecutively linked together in the presence of the peptide linker.

In addition, the peptide linker may be linked to the N-terminal and/or C-terminal end of the polypeptide. In particular, when a peptide linker is linked to both the N-terminal and C-terminal of the polypeptide, each peptide linker may include a cysteine. For example, when the cysteines are respectively linked to the N-terminal and C-terminal of the polypeptide, a disulfide bond may be formed between the two cysteines so that the polypeptide may exist between them, which can form a circular polypeptide including the polypeptide that inhibits binding between VEGFR-2 and a VEGF.

The Fc region of the antibody may be derived from an animal selected from the group consisting of a human, a mouse, a rabbit, and a goat.

In an embodiment, the inhibitor polypeptide or the fusion protein including the same may specifically bind a region of VEGFR-2 to which the VEGF is bound to inhibit the binding between VEGFR-2 and VEGF. For example, the inhibition of the binding between VEGFR-2 and VEGF may be carried out in such a way that the inhibitor polypeptide or the fusion protein including the same binds an extracellular region of VEGFR-2 to prevent the VEGF from binding to the region of VEGFR-2. The inhibition of the binding between VEGFR-2 and VEGF by the inhibitor polypeptide or the fusion protein including the same may also be carried out in such a way that transduction of intracellular signals generated by the binding between VEGFR-2 and the VEGF are blocked, for example, signals resulting in angiogenesis.

According to an embodiment of the present invention, there is provided a polynucleotide encoding a fusion protein including a polypeptide that has an amino acid sequence represented by Formula I above and inhibits binding between VEGFR-2 and a VEGF; and an Fc region of an antibody.

The polynucleotide may have a nucleotide sequence selected from the group consisting of SEQ ID NOS: 14 through 16.

According to an embodiment of the present invention, there is provided a polynucleotide encoding a fusion protein including a polypeptide that has one amino acid sequence selected from the group consisting of SEQ ID NOS: 4 through 13 and inhibits binding between VEGFR-2 and a VEGF; and an Fc region of an antibody.

The polynucleotide may have a nucleotide sequence selected from the group consisting of SEQ ID NOS: 17 through 26.

The fusion protein encoded by the polynucleotide may further include a linker that links the polypeptide to the Fc region of the antibody.

The term "polynucleotide" used herein refers to a polymer of deoxyribonucleotide or ribonucleotide that exists in a single-stranded or double-stranded form. The polynucleotide generally includes RNA genome sequences, DNA (gDNA and cDNA), and RNA sequences transcribed therefrom, and includes analogues of natural polynucleotide.

The polynucleotide includes a nucleotide sequence encoding the amino acid sequence of the fusion protein or a nucleotide sequence complementary thereto. The complementary sequences include completely complementary sequences and substantially complementary sequences. For example, a complementary sequence indicates a sequence that may be hybridized with the nucleotide sequence encoding the amino acid sequence of the fusion protein under stringent conditions known in the art. Specifically, stringent conditions mean, for example, hybridization to DNA in 6×SSC at about 45° C., followed by one or more washes in 0.2×SSC/0.1% SDS at about 50° C.-65° C.

"Isolated," when used to describe the various polypeptides, fusion proteins, or polynucleotides disclosed herein, means a polypeptide, fusion protein, or polynucleotide that has been identified and separated and/or recovered from a component of its natural environment. The term also embraces recombinant polynucleotides and polypeptides and chemically synthesized polynucleotides and polypeptides.

According to an embodiment of the present invention, there is provided a recombinant vector including a polynucleotide encoding a fusion protein including a polypeptide that has an amino acid sequence represented by Formula I above and that inhibits binding between VEGFR-2 and a VEGF; and an Fc region of an antibody, and a promoter operatively linked to the sequence of the polynucleotide.

According to an embodiment of the present invention, there is provided a recombinant vector including a polynucleotide encoding a fusion protein including a polypeptide that has one amino acid sequence selected from the group consisting of SEQ ID NOS: 4 through 13 and that inhibits binding between VEGFR-2 and a VEGF; and an Fc region of an antibody, and a promoter operatively linked to the sequence of the polynucleotide.

The encoded fusion protein may further include a linker that links the polypeptide to the Fc region of the antibody.

The term "vector" used herein refers to a polynucleotide for expressing a target gene in a host cell. For example, the vector may include a plasmid vector, a cosmid vector, and a virus vector, such as a bacteriophage vector, an adenovirus vector, a retrovirus vector, and an adeno-associated virus vector. The recombinant vector may be prepared by manipulating a plasmid known in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), a phage (for example, λgt4λB, λ-Charon, λΔz1, and M13), or a virus (for example, SV40).

In the recombinant vector, the sequence of the polynucleotide encoding the fusion protein may be operatively linked to a promoter. The term "operatively linked" used herein means a functional linkage between a nucleotide expression regulating sequence (for example, a promoter sequence) and other nucleotide sequences. Thus, the nucleotide expression regulating sequence may regulate the transcription and/or translation of the other nucleotide sequences.

The recombinant vector may be an expression vector, which may stably express the fusion protein in a host cell. The expression vector may be a vector commonly used in the art for expressing foreign protein in a plant, animal or microorganism. The recombinant vector may be constructed using various methods known in the art.

The recombinant vector may be constructed for use in prokaryotic or eukaryotic host cells. For example, when a prokaryotic cell is used as a host cell, the expression vector used generally includes a strong promoter capable of initiating transcription (for example, $p_L^\lambda$ promoter, trp promoter, lac promoter, tac promoter, T7 promoter), a ribosome binding site for initiating translation, and a transcription/translation termination sequence. When a eukaryotic cell is used as a host cell, the vector can include an origin of replication acting in the eukaryotic cell. The origin of replication can be, e.g., f1 origin of replication, SV40 origin of replication, pMB1 origin of replication, adeno origin of replication, AAV origin of replication, or BBV origin of replication, but is not limited thereto. The promoter in an expression vector for a eukaryotic host cell may be a promoter derived from genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). The transcription termination sequence in an expression vector for a eukaryotic host cell may be, in general, a polyadenylation sequence.

According to an embodiment of the present invention, there is provided a cell including a polynucleotide encoding a fusion protein including a polypeptide that has an amino acid sequence represented by Formula I above and that inhibits binding between VEGFR-2 and a VEGF; and an Fc region of an antibody.

According to an embodiment of the present invention, there is provided a cell including a polynucleotide encoding a fusion protein including a polypeptide that has one amino acid sequence selected from the group consisting of SEQ ID NOS: 4 through 13 and that inhibits binding between VEGFR-2 and a VEGF; and an Fc region of an antibody.

The encoded fusion protein may further include a linker that links the polypeptide to the Fc region of the antibody.

The cell may be transformed with the polynucleotide encoding the fusion protein or with the recombinant vector including the polynucleotide and a promoter operatively linked to the sequence of the polynucleotide.

In other words, the cell may include the sequence of the polynucleotide encoding a fusion protein on the genome of the host cell, or a recombinant vector with the polynucleotide sequence included therein.

The cell, which is capable of stably and consecutively cloning or expressing the recombinant vector, may be any host cell known in the art. The prokaryotic cell may be a *Bacillus* genus bacterial cell, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*, intestinal bacteria, such as *Salmonella typhimurium, Serratia marcescens*, and various *Pseudomonas* species. A eukaryotic host cell may be a yeast (*Saccharomyce cerevisiae*), an insect cell, a plant cell, or an animal cell, for example, a CHO (Chinese hamster ovary), W138, BHK, COS-7, 293, HepG2, 3T3, RIN, or a MDCK cell.

The polynucleotide or the recombinant vector including the same may be transferred into the host cell by using a method known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

The transformed host cell may be selected using a phenotype expressed by a selectable marker by known methods in the art. For example, when the selectable marker is a specific antibiotic resistance gene, a transformant is cultured in a medium including the antibiotic, and thus the transformant may easily be selected.

According to an embodiment of the present invention, there is provided a method of preparing a fusion protein, the method including culturing a cell having a polynucleotide encoding a fusion protein including a polypeptide that has an amino acid sequence represented by Formula I above and that inhibits binding between VEGFR-2 and a VEGF; and an Fc region of an antibody; and collecting protein expressed from the culture.

According to an embodiment of the present invention, there is provided a method of preparing a fusion protein, the method including culturing a cell having a polynucleotide encoding a fusion protein including a polypeptide that has one amino acid sequence selected from the group consisting of SEQ ID NOS: 4 through 13 and that inhibits binding between VEGFR-2 and a VEGF; and an Fc region of an antibody; and collecting protein expressed from the culture.

The fusion protein may further include a linker that links the polypeptide to the Fc region of the antibody.

The transformed host cell may be cultured using various known methods. For example, a transformed host cell with fusion protein expression under the control of the lacZ promoter can be inoculated into LB liquid medium including an appropriate antibiotic and cultured therein. Isopropyl β-D-1-thiogalactopyranoside (IPTG) can be added to the LB liquid medium to induce protein expression by the lacZ promoter at a time when the cell density reaches a certain level. After culturing the cells, protein expressed within the cell or secreted to the culture medium may be collected.

The protein expressed inside the cell or secreted into the medium may be obtained in a purified form by using one of various known purification methods in the art. Examples of purification methods include solubility fractionation by use of ammonium sulphate, size differential filtration, and various chromatography methods (performing separation according to size, charge, hydrophobicity or affinity). For example, if the fusion protein includes glutathione-S-transferase (GST), the protein may easily be obtained using a glutathione-binding resin column, or if the fusion protein includes a 6×His sequence, the protein may easily be obtained using a $Ni^{2+}$-NTA His-binding resin column.

According to an embodiment of the present invention, there is provided a composition for preventing or treating angiogenesis-related diseases or cancer. The composition includes a fusion protein including a polypeptide that has one amino acid sequence selected from the group consisting of an amino acid sequence represented by Formula I above and amino acid sequences of SEQ ID NOS: 4 through 13, and that inhibits binding between VEGFR-2 and VEGF; and a Fc region of an antibody; and a pharmaceutically acceptable carrier. The fusion protein may be present in a therapeutically effective amount.

The fusion protein may further include a linker that links the polypeptide to the Fc region of the antibody.

The composition may be used to prevent or treat cancer. Examples of cancers are carcinoma, lymphoma, blastoma, sarcoma, and leukemia. In particular, the cancer may be squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, or various types of head and neck cancers, but is not limited thereto.

In addition, the composition may be used to prevent or treat an angiogenesis-related disease. Angiogenesis is a physiological process involving the formation of new capillary vessels from pre-existing vessels. If the angiogenesis is not regulated autonomously, the vessels grow abnormally, causing diseases. Examples of angiogenesis-related diseases are rheumatoid arthritis, osteoarthritis, septic arthritis, psoriasis, corneal ulcer, age-related macular degeneration, diabetic retinopathy, proliferative vitreoretinopathy, premature retinopathy, keratoconus, Sjogren's syndrome, myopia ocular tumors, corneal graft rejection, abnormal wound healing, bone diseases, proteinuria, abdominal aortic aneurysm diseases, degenerative cartilage loss due to traumatic joint damage, nervous system demyelination diseases, liver cirrhosis, glomerular disease, premature rupture of embryonic membranes, inflammatory bowel disease, periodontal disease, arteriosclerosis, restenosis, central nervous system inflammation diseases, Alzheimer's disease, skin aging, and cancer invasion and metastasis, but are not limited thereto.

The composition for preventing or treating angiogenesis-related diseases or cancers includes a pharmaceutically acceptable carrier. The pharmaceutically acceptable carrier, which is commonly used in formulation, may be lactose, dextrose, sucrose, sorbitol, mannitol, starch, gum acacia, calcium phosphate, alginates, gelatin, calcium silicate, microcrystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include a lubricant, a wetting agent, a sweetener, a flavor enhancer, an emulsifying agent, a suspension agent, and a preservative.

The composition for preventing or treating an angiogenesis-related disease or cancer may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration can lead to digestion of protein or peptide, the composition may be coated or the composition may be formulated to prevent the digestion. In addition, the composition may be administered by using a device capable of transferring an active material to a target cell.

A suitable dose of the composition for preventing or treating an angiogenesis-related disease or cancer may depend on many factors, such as formulation methods, administration methods, age of patients, body weight, gender, pathologic conditions, diets, administration time, administration route, excretion speed, and reaction sensitivity. A desirable dose of the composition may be in the range of about 0.001 to about 100 mg/kg for an adult. The term "therapeutically effective amount" used herein refers to a sufficient amount used in preventing or treating cancer or an angiogenesis-related disease.

The composition may be formulated using a pharmaceutically acceptable carrier and/or an additive by a known method in the art and prepared in a unit dose form or be contained in a multi-dose container. In this regard, the formulation may be a solution in oil or an aqueous medium, a suspension, a syrup, an emulsifying solution, an extract, powder, granules, a tablet, or a capsule, and may further include a dispersing or a stabilizing agent. In addition, the composition may be administered as an individual drug, or together with other drugs, and may be administered sequentially or simultaneously with other drugs.

According to an embodiment of the present invention, there is provided a method of treating an angiogenesis-related disease or cancer of an animal, the method including administering to a subject a therapeutically effective amount of a fusion protein including: a polypeptide that has one amino acid sequence selected from the group consisting of an amino acid sequence represented by Formula I above and amino acid sequences of SEQ ID NOS: 4 through 13 and that inhibits binding between VEGFR-2 and VEGF; and a Fc region of an antibody. The fusion protein can be in the form of a composition including a pharmaceutically acceptable carrier.

The fusion protein may further include a linker that links the polypeptide to the Fc region of the antibody.

A detailed description of the composition for preventing or treating an angiogenesis-related disease or cancer and the administration method thereof has been provided above.

The subject to which the fusion protein is administered includes animals. For example, the animals may be humans, dogs, cats, or mice.

One or more embodiments of the present invention will now be described in further detail with reference to the following examples. However, these examples are for illustrative purposes only and are not intended to limit the scope of the invention.

EXAMPLE 1

Screening for Polypeptides Specifically Binding to VEGFR-2

Figure 1:
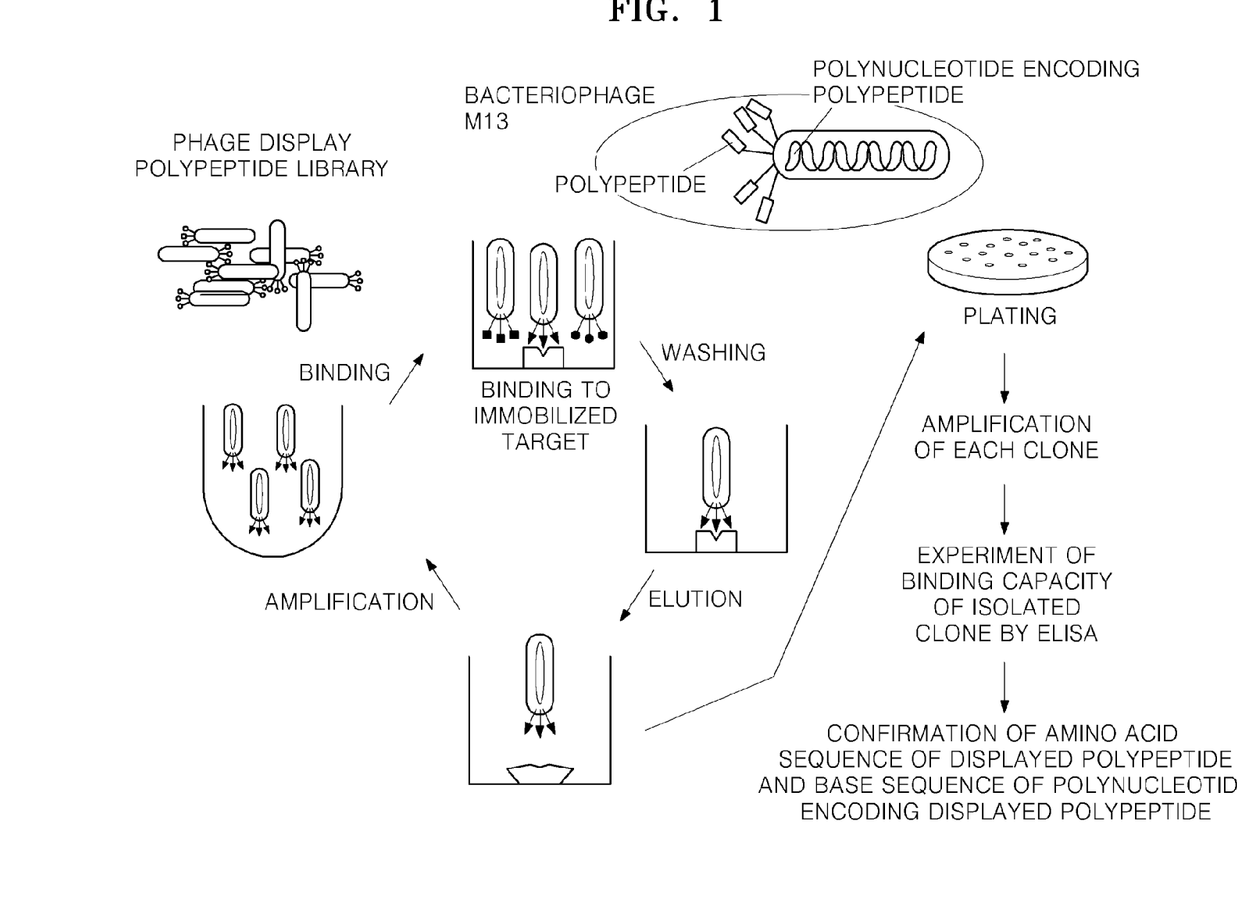
FIG. 1 is a schematic flowchart illustrating a process of screening for a polypeptide inhibiting binding between vascular endothelial growth factor receptor-2 and a vascular endothelial growth factor, according to an embodiment of the present invention.

FIG. 1 presents a schematic illustration of a process for screening for polypeptides specifically binding to VEGFR-2.

(1) Biopanning

Human VEGFR-2 (R&D systems, Inc.; catalog #357-KD) was immobilized on an appropriate solid surface (for example, a plate), a phage display polypeptide library (Dyax) was added thereto to be bound to the VEGFR-2, and under various binding times and washing conditions, polypeptide expression phages binding to VEGFR-2 with high binding affinity were selected.

The biopanning was performed using bead panning. In particular, magnetic beads with streptavidin attached to the bead surface and VEGFR-2 with biotin bound thereto were mixed together, and then the mixture was stirred at 4° C. for 18 hours to immobilize the VEGFR-2 to the surface of the magnetic beads. The magnetic beads with the VEGFR-2 immobilized thereon were blocked with skim milk at room temperature for two hours, and then a polypeptide displaying phage solution was added to the magnetic beads. The mixture was stirred for reaction for two hours, and washed using a phosphate buffered saline (PBS) solution (1.06 mM $KH_2PO_4$, 155.17 mM NaCl, 2.97 mM $Na_2HPO_4$-$7H_2O$) and a PBS solution including 0.1% Tween-20. Then, the phages bound to the VEGFR-2 immobilized on the beads were separated from the solution. The biopanning process was performed up to two or three times depending upon the number of phages obtained after the biopanning process.

(2) Phage ELISA and Determination of Sequences of Polynucleotides Encoding the Polypeptides Specifically Binding to VEGFR-2 and Sequences of the Polypeptides

*E. coli* XL1-Blue was infected with phage clones obtained from the biopanning process, and the cells were cultured at 37° C. for about 12 hours to about 16 hours to obtain a phage solution. VEGFR-2 was added to a 96-well microtiter plate (Nunc), and maintained at 4° C. for 18 hours to immobilize the protein on a surface of the plate. The plate with the immobilized VEGFR-2 was blocked at room temperature for 1 hour, and 100 μl of the phage solution was added to the plate. Then, the phage and the VEGFR-2 were incubated together at room temperature for two hours, and washed using a PBS solution containing 0.1% Tween-20. Subsequently, an anti-M13 antibody (GE Healthcare) specifically reactive to the phage and conjugated with horseradish peroxidase (HRP) was added to the resultant product and incubated at room temperature for 1 hour. Then, the plate was washed twice with a PBS solution containing 0.1% Tween-20. Lastly, 100 μl of trimethylbenzidine (TMB)(SIGMA), an HRP substrate, was added to each well of the plate to induce a color reaction. The reaction was stopped by adding 50 μl of $5NH_2SO_4$ solution. The $OD_{450}$ value was read on a plate reader (Molecular Devices). From the results, a total of 13 phage clones were identified as having a high binding affinity with VEGFR-2. To determine the base sequence of polynucleotides encoding the polypeptides specifically binding to VEGFR-2 obtained from single clones of the phages, a colony polymerase chain reaction (PCR) was performed using various primer sets: SEQ ID NOS: 27 and 28; SEQ ID NOS: 29 and 30; SEQ ID NOS: 31 and 32; SEQ ID NOS: 33 and 34; SEQ ID NOS: 35 and 36. Each primer set was used according to the origin of the Dyax polypeptide library. For example, the primer set having SEQ ID NOS: 27 and 28 was used to confirm that the encoded number of amino acids of a polypeptide displayed in a phage is 4, and the primer set having SEQ ID NOS: 29 and 30 was used to confirm that the encoded number of amino acids of a polypeptide displayed in a phage is 5, 6, or 7. The PCR was performed using a GeneAmp PCR system 9700 (Applied Biosystem), with the following PCR conditions: 30 cycles of 94° C. for 5 minutes, 94° C. for 1 minute, 60° C. for 1 minute, and 72° C. for 1.5 minutes; 72° C. for 10 minutes; and cooling to 4° C. Subsequently, polynucleotide fragments obtained by the PCR reaction were washed and then sequenced (Solgent). The amino acid sequence of the polypeptide specifically binding to VEGFR-2 was determined from the sequence of the polynucleotide encoding the polypeptide (refer to Table 1). Table 1 below shows amino acid sequences of the regions of the polypeptides displayed in the phage that specifically binding to the VEGFR-2 and the polynucleotide base sequences encoding the polypeptide regions.

TABLE 1

| Polypeptide number | Amino acid sequence | Base sequence of polypeptide cDNA |
|---|---|---|
| 9 | HIKAGQWF (SEQ ID NO: 1) | catattaaggctggtcagtggttt (SEQ ID NO: 14) |
| 10 | HINAGQWF (SEQ ID NO: 2) | catattaatgctggtcagtggttt (SEQ ID NO: 15) |
| 11 | HITDGQWF (SEQ ID NO: 3) | catattacggatggtcagtggttt (SEQ ID NO: 16) |
| 19 | IDVS (SEQ ID NO: 4) | attgatgtttct (SEQ ID NO: 17) |
| 20 | LLPSG (SEQ ID NO: 5) | cttcttccttctggt (SEQ ID NO: 18) |
| 5 | GYEWQY (SEQ ID NO: 6) | ggttatgagtggcagtat (SEQ ID NO: 19) |
| 8 | DGSGPPTN (SEQ ID NO: 7) | gatggttctggtcctcctactaat (SEQ ID NO: 20) |
| 12 | WSLGRPFP (SEQ ID NO: 8) | tggtctcttggtcgtccttttcct (SEQ ID NO: 21) |
| 13 | KHKNQATG (SEQ ID NO: 9) | aagcataagaatcaggctactggt (SEQ ID NO: 22) |
| 14 | WAIHKPWP (SEQ ID NO: 10) | tgggctattcataagccttggcct (SEQ ID NO: 23) |
| 15 | YQDKSHGGF (SEQ ID NO: 11) | tatcaggataagtctcatggtggtttt (SEQ ID NO: 24) |
| 16 | FEGTYGGEV (SEQ ID NO: 12) | tttgagggtacttatggtggtgaggtt (SEQ ID NO: 25) |
| 17 | HLNMRYQWI (SEQ ID NO: 13) | catcttaatatgcgttatcagtggatt (SEQ ID NO: 26) |

A polynucleotide encoding the polypeptide obtained according to Example 1 was cloned into a vector expressing an Fc region of a human antibody. The vector used has a cytomegalovirus (CMV) promoter, and a polynucleotide encoding the Fc region of a human antibody. The polynucleotide encoding a polypeptide of Example 1 was cloned into the vector such that it was linked to the 3' end of the polynucleotide encoding the Fc region of the human antibody. Thus, in the expressed fusion protein, the polypeptide of Example 1 was linked to the C-terminal end of the polypeptide constituting the Fc region of the human antibody. In particular, the polynucleotide encoding a polypeptide of Example 1 and the vector were respectively digested with restriction enzymes, i.e., Not I (Roche) and Xba I (Roche), and the resultant products were ligated with each other by using a T4 DNA lagase (NEB) to prepare a vector for expressing a peptibody including the desired polypeptide region. The prepared recombinant vectors were transfected into HEK-293E cells distributed by the Korean Research Institute of Biotechnology. To express the fusion protein, the HEK-293E cells were cultured in serum-free Dulbecco's Modified Eagle Medium (DMEM) (Invitrogen), which was changed four times at intervals of three days. The fusion protein including the polypeptide having the amino acid sequence of Table 1 was confirmed to be expressed in the culture medium.

EXAMPLE 2

Determination of Fusion Protein Ability to Inhibit Binding Between VEGF and VEGFR-2

Competitive ELISA was used to evaluate the ability of the fusion proteins to inhibit binding between VEGF and VEGFR-2.

0.5 μg/ml of VEGFR-2 (R&D Systems) was immobilized on a 96-well MaxiSorp™ flat-bottom plate (Nunc), the plate was washed with PBS containing 0.1% Tween-20 five times, and then the plate was blocked with PBS containing 5% bovine serum albumin (BSA) at room temperature for 2 hours. Culture medium including a fusion protein prepared according to Example 1 was diluted to 1:2, 1:8, 1:32, 1:128, and 1:512 and 100 μl of the diluted culture medium was added to each well and left to incubate at room temperature for two hours. Subsequently, 0.01 μg/ml of VEGF (R&D Systems) was added to each well and the resultant product was incubated at room temperature for two hours. After the reaction was terminated, the plate was washed five times with PBS containing 0.1% Tween-20. Anti-VEGF mouse antibodies (R&D Systems) were diluted to 1:5,000 with PBS containing 1% BSA, added to the plate wells, and incubated at room temperature for one hour. Then, 100 μl of goat anti-mouse-IgG-HRP (Pierce), diluted with PBS containing 1% BSA to a ratio of about 1:5,000, was added to each well of the plate, incubated at room temperature for one hour, and washed five times with PBS containing 0.1% Tween-20.

Lastly, 100 μl of trimethylbenzidine (TMB) substrate (SIGMA) was added to each well of the plate to induce a color reaction. The reaction was stopped by adding 50 μl of 5N $H_2SO_4$ solution. The $OD_{450}$ value was read on a plate reader (Molecular Devices).

Figure 2:
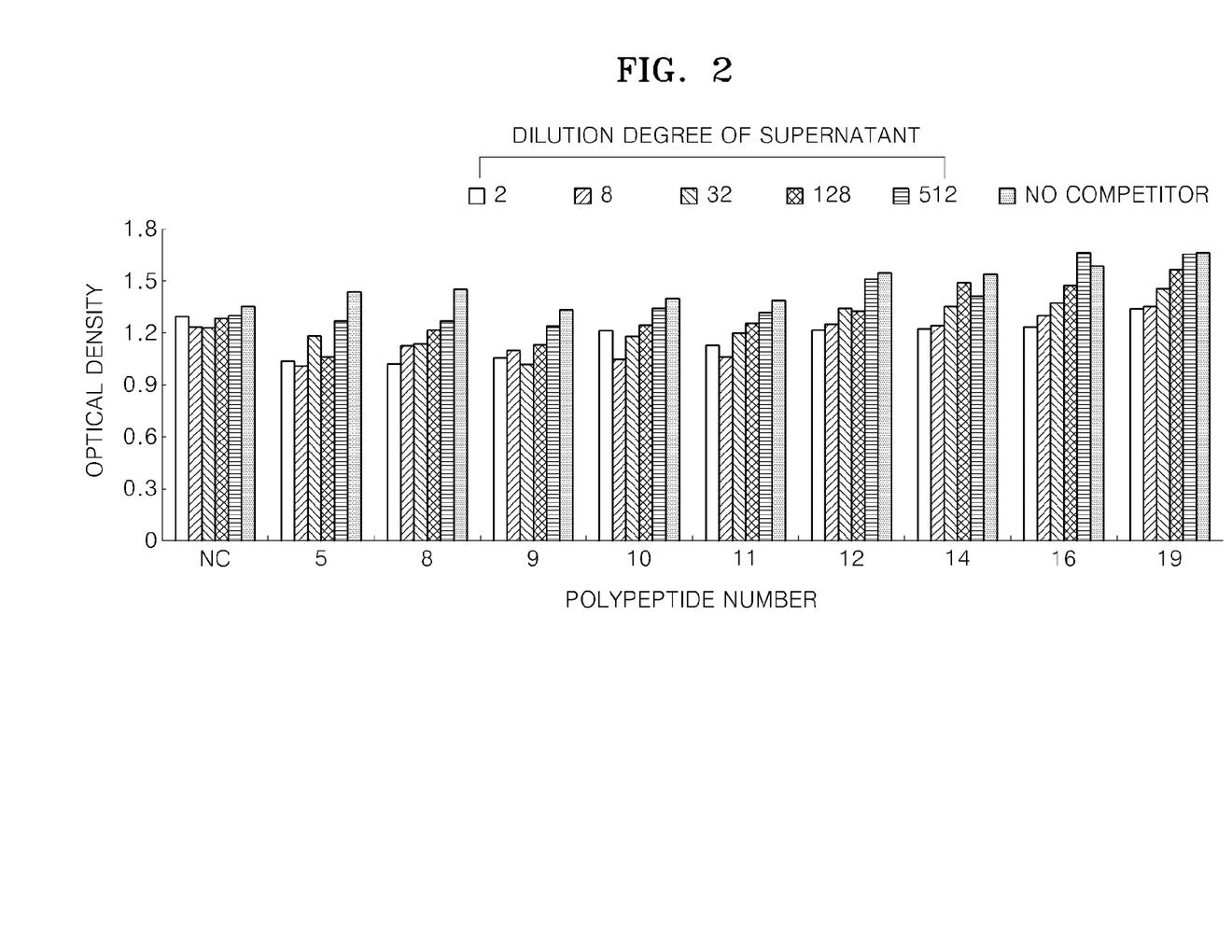
FIG. 2 is a histograph showing competitive enzyme-linked immunosorbent assay (ELISA) results measuring the ability of various fusion proteins disclosed herein to inhibit binding between vascular endothelial growth factor receptor-2 and a vascular endothelial growth factor.

Referring to FIG. 2, it can be seen that fusion proteins containing a polypeptide shown in Table 1 are capable of inhibiting binding between VEGF and VEGFR-2. In FIG. 2, the X axis corresponds to the VEGFR2 binding polypeptide number ("polypeptide number" of Table 1) or a negative control (NC), aFc-fusion protein linked to a polypeptide which does not bind to VEGFR2, while the Y axis is optical density at 450 nm. The key to the various dilution factors tested is shown at the top of the histogram.

As described above, according to one or more embodiments of the present invention, an inhibitor polypeptide specifically binding to VEGFR-2 or specifically inhibiting VEGFR-2/VEGF binding, a fusion protein comprising the inhibitor polypeptide, and a composition for preventing or treating an angiogenesis-related disease or cancer cancer are disclosed and may efficiently prevent or treat an angiogenesis-related disease or cancer. Polynucleotides, recombinant vectors, and host cells to express the inhibitor polypeptide or fusion protein are also disclosed.

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. An isolated polypeptide consisting of an amino acid sequence of Formula I below, which inhibits binding between vascular endothelial cell growth factor receptor-2 and a vascular endothelial growth factor:

<Formula I>
His-Ile-$X_1$-$X_2$-Gly-Gln-Trp-Phe (SEQ ID NO: 37)

wherein $X_1$ denotes an amino acid selected from the group consisting of Asn, Thr, and Lys, and $X_2$ denotes an amino acid selected from the group consisting of Ala and Asp.

2. The polypeptide of claim 1, consisting of an amino acid sequence selected from the group consisting of SEQ ID NO: 1, SEQ ID NO: 2, and SEQ ID NO: 3.

3. An isolated fusion protein comprising: a polypeptide having an amino acid sequence of Formula I below which inhibits binding between vascular endothelial growth factor receptor-2 and a vascular endothelial growth factor; and an Fc region of an antibody:

<Formula I>
His-Ile-$X_1$-$X_2$-Gly-Gln-Trp-Phe (SEQ ID NO: 37)

wherein $X_1$ denotes an amino acid selected from the group consisting of Asn, Thr, and Lys, and $X_2$ denotes an amino acid selected from the group consisting of Ala and Asp.

4. The fusion protein of claim 3, wherein the polypeptide inhibiting binding between vascular endothelial growth factor receptor-2 and a vascular endothelial growth factor has an amino acid sequence selected from the group consisting of SEQ ID NOS: 1 through 3.

5. The fusion protein of claim 3, further comprising a linker that links the polypeptide to the Fc region of the antibody.

6. The fusion protein of claim 3, wherein the Fc region of the antibody is derived from an animal selected from the group consisting of a human, a mouse, a rabbit, and a goat.

7. An isolated polynucleotide encoding a fusion protein comprising: a polypeptide having an amino acid sequence of Formula I below, which inhibits binding between vascular endothelial growth factor receptor-2 and a vascular endothelial growth factor; and an Fc region of an antibody:

<Formula I>
His-Ile-$X_1$-$X_2$-Gly-Gln-Trp-Phe (SEQ ID NO: 37)

wherein $X_1$ denotes an amino acid selected from the group consisting of Asn, Thr, and Lys, and $X_2$ denotes an amino acid selected from the group consisting of Ala and Asp.

8. The polynucleotide of claim 7, having a nucleotide sequence selected from the group consisting of SEQ ID NOS: 14 through 16.

9. A recombinant vector comprising the polynucleotide of claim 7, and a promoter operatively linked to a sequence of the polynucleotide.

10. A host cell comprising the polynucleotide of claim 7.

11. A method of preparing a fusion protein, the method comprising
culturing the host cell of claim 10 under conditions that allow expression of the fusion protein; and
collecting protein expressed from the culture.

* * * * *

SEQUENCE LISTING

```
<160> NUMBER OF SEQ ID NOS: 37

<210> SEQ ID NO 1
<211> LENGTH: 8
<212> TYPE: PRT
<213> ORGANISM: Artificial Sequence
<220> FEATURE:
<223> OTHER INFORMATION: polypeptide binding specifically to VEGFR-2

<400> SEQUENCE: 1

His Ile Lys Ala Gly Gln Trp Phe
 1               5

<210> SEQ ID NO 2
<211> LENGTH: 8
<212> TYPE: PRT
<213> ORGANISM: Artificial Sequence
<220> FEATURE:
<223> OTHER INFORMATION: polypeptide binding specifically to VEGFR-2

<400> SEQUENCE: 2

His Ile Asn Ala Gly Gln Trp Phe
 1               5

<210> SEQ ID NO 3
<211> LENGTH: 8
<212> TYPE: PRT
<213> ORGANISM: Artificial Sequence
<220> FEATURE:
<223> OTHER INFORMATION: polypeptide binding specifically to VEGFR-2

<400> SEQUENCE: 3

His Ile Thr Asp Gly Gln Trp Phe
 1               5

<210> SEQ ID NO 4
<211> LENGTH: 4
<212> TYPE: PRT
<213> ORGANISM: Artificial Sequence
<220> FEATURE:
<223> OTHER INFORMATION: polypeptide binding specifically to VEGFR-2

<400> SEQUENCE: 4
```

Ile Asp Val Ser
1

<210> SEQ ID NO 5
<211> LENGTH: 5
<212> TYPE: PRT
<213> ORGANISM: Artificial Sequence
<220> FEATURE:
<223> OTHER INFORMATION: polypeptide binding specifically to VEGFR-2

<400> SEQUENCE: 5

Leu Leu Pro Ser Gly
1               5

<210> SEQ ID NO 6
<211> LENGTH: 6
<212> TYPE: PRT
<213> ORGANISM: Artificial Sequence
<220> FEATURE:
<223> OTHER INFORMATION: polypeptide binding specifically to VEGFR-2

<400> SEQUENCE: 6

Gly Tyr Glu Trp Gln Tyr
1               5

<210> SEQ ID NO 7
<211> LENGTH: 8
<212> TYPE: PRT
<213> ORGANISM: Artificial Sequence
<220> FEATURE:
<223> OTHER INFORMATION: polypeptide binding specifically to VEGFR-2

<400> SEQUENCE: 7

Asp Gly Ser Gly Pro Pro Thr Asn
1               5

<210> SEQ ID NO 8
<211> LENGTH: 8
<212> TYPE: PRT
<213> ORGANISM: Artificial Sequence
<220> FEATURE:
<223> OTHER INFORMATION: polypeptide binding specifically to VEGFR-2

<400> SEQUENCE: 8

Trp Ser Leu Gly Arg Pro Phe Pro
1               5

<210> SEQ ID NO 9
<211> LENGTH: 8
<212> TYPE: PRT
<213> ORGANISM: Artificial Sequence
<220> FEATURE:
<223> OTHER INFORMATION: polypeptide binding specifically to VEGFR-2

<400> SEQUENCE: 9

Lys His Lys Asn Gln Ala Thr Gly
1               5

<210> SEQ ID NO 10
<211> LENGTH: 8
<212> TYPE: PRT
<213> ORGANISM: Artificial Sequence
<220> FEATURE:
<223> OTHER INFORMATION: polypeptide binding specifically to VEGFR-2

<400> SEQUENCE: 10

Trp Ala Ile His Lys Pro Trp Pro
1               5

```
<210> SEQ ID NO 11
<211> LENGTH: 9
<212> TYPE: PRT
<213> ORGANISM: Artificial Sequence
<220> FEATURE:
<223> OTHER INFORMATION: polypeptide binding specifically to VEGFR-2

<400> SEQUENCE: 11

Tyr Gln Asp Lys Ser His Gly Gly Phe
 1               5

<210> SEQ ID NO 12
<211> LENGTH: 9
<212> TYPE: PRT
<213> ORGANISM: Artificial Sequence
<220> FEATURE:
<223> OTHER INFORMATION: polypeptide binding specifically to VEGFR-2

<400> SEQUENCE: 12

Phe Glu Gly Thr Tyr Gly Gly Glu Val
 1               5

<210> SEQ ID NO 13
<211> LENGTH: 9
<212> TYPE: PRT
<213> ORGANISM: Artificial Sequence
<220> FEATURE:
<223> OTHER INFORMATION: polypeptide binding specifically to VEGFR-2

<400> SEQUENCE: 13

His Leu Asn Met Arg Tyr Gln Trp Ile
 1               5

<210> SEQ ID NO 14
<211> LENGTH: 24
<212> TYPE: DNA
<213> ORGANISM: Artificial Sequence
<220> FEATURE:
<223> OTHER INFORMATION: polynucleotide encoding polypeptide binding
      specifically to VEGFR-2

<400> SEQUENCE: 14
catattaagg ctggtcagtg gttt                                          24

<210> SEQ ID NO 15
<211> LENGTH: 24
<212> TYPE: DNA
<213> ORGANISM: Artificial Sequence
<220> FEATURE:
<223> OTHER INFORMATION: polynucleotide encoding polypeptide binding
      specifically to VEGFR-2

<400> SEQUENCE: 15
catattaatg ctggtcagtg gttt                                          24

<210> SEQ ID NO 16
<211> LENGTH: 24
<212> TYPE: DNA
<213> ORGANISM: Artificial Sequence
<220> FEATURE:
<223> OTHER INFORMATION: polynucleotide encoding polypeptide binding
      specifically to VEGFR-2

<400> SEQUENCE: 16
catattacgg atggtcagtg gttt                                          24
```

<210> SEQ ID NO 17
<211> LENGTH: 12
<212> TYPE: DNA
<213> ORGANISM: Artificial Sequence
<220> FEATURE:
<223> OTHER INFORMATION: polynucleotide encoding polypeptide binding specifically to VEGFR-2

<400> SEQUENCE: 17
attgatgttt ct                                                    12

<210> SEQ ID NO 18
<211> LENGTH: 15
<212> TYPE: DNA
<213> ORGANISM: Artificial Sequence
<220> FEATURE:
<223> OTHER INFORMATION: polynucleotide encoding polypeptide binding specifically to VEGFR-2

<400> SEQUENCE: 18
cttcttcctt ctggt 15

<210> SEQ ID NO 19
<211> LENGTH: 18
<212> TYPE: DNA
<213> ORGANISM: Artificial Sequence
<220> FEATURE:
<223> OTHER INFORMATION: polynucleotide encoding polypeptide binding specifically to VEGFR-2

<400> SEQUENCE: 19
ggttatgagt ggcagtat 18

<210> SEQ ID NO 20
<211> LENGTH: 24
<212> TYPE: DNA
<213> ORGANISM: Artificial Sequence
<220> FEATURE:
<223> OTHER INFORMATION: polynucleotide encoding polypeptide binding specifically to VEGFR-2

<400> SEQUENCE: 20
gatggttctg gtcctcctac taat 24

<210> SEQ ID NO 21
<211> LENGTH: 24
<212> TYPE: DNA
<213> ORGANISM: Artificial Sequence
<220> FEATURE:
<223> OTHER INFORMATION: polynucleotide encoding polypeptide binding specifically to VEGFR-2

<400> SEQUENCE: 21
tggtctcttg gtcgtccttt tcct 24

<210> SEQ ID NO 22
<211> LENGTH: 24
<212> TYPE: DNA
<213> ORGANISM: Artificial Sequence
<220> FEATURE:
<223> OTHER INFORMATION: polynucleotide encoding polypeptide binding specifically to VEGFR-2

<400> SEQUENCE: 22
aagcataaga atcaggctac tggt 24

<210> SEQ ID NO 23
<211> LENGTH: 24

```
<212> TYPE: DNA
<213> ORGANISM: Artificial Sequence
<220> FEATURE:
<223> OTHER INFORMATION: polynucleotide encoding polypeptide binding
      specifically to VEGFR-2

<400> SEQUENCE: 23
tgggctattc ataagccttg gcct                                          24

<210> SEQ ID NO 24
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGFR-2

<400> SEQUENCE: 24
tatcaggata agtctcatgg tggtttt                                       27

<210> SEQ ID NO 25
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGFR-2

<400> SEQUENCE: 25
tttgagggta cttatggtgg tgaggtt                                       27

<210> SEQ ID NO 26
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGFR-2

<400> SEQUENCE: 26
catcttaata tgcgttatca gtggatt                                       27

<210> SEQ ID NO 27
<211> LENGTH: 27
<212> TYPE: DNA
<213> ORGANISM: Artificial Sequence
<220> FEATURE:
<223> OTHER INFORMATION: TN6-forward primer

<400> SEQUENCE: 27
ggaggaagcg gccgcggtac tggcagc                                       27

<210> SEQ ID NO 28
<211> LENGTH: 26
<212> TYPE: DNA
<213> ORGANISM: Artificial Sequence
<220> FEATURE:
<223> OTHER INFORMATION: TN6-reverse primer

<400> SEQUENCE: 28
cctcctctct agagcggacc aggagc                                        26

<210> SEQ ID NO 29
<211> LENGTH: 27
<212> TYPE: DNA
<213> ORGANISM: Artificial Sequence
<220> FEATURE:
<223> OTHER INFORMATION: TN7,8,9-forward primer
```

<400> SEQUENCE: 29
ggaggaagcg gccgcsgymc yggyrry					27

<210> SEQ ID NO 30
<211> LENGTH: 26
<212> TYPE: DNA
<213> ORGANISM: Artificial Sequence
<220> FEATURE:
<223> OTHER INFORMATION: TN7,8,9-reverse primer
<220> FEATURE:
<221> NAME/KEY: misc_difference
<222> LOCATION: (15)
<223> OTHER INFORMATION: "n" represents any of nucleotide A, G, T or C
<220> FEATURE:
<221> NAME/KEY: misc_difference
<222> LOCATION: (24)
<223> OTHER INFORMATION: "n" represents any of nucleotide A, G, T or C

<400> SEQUENCE: 30
cctcctctct agagnggytc mgtncc					26

<210> SEQ ID NO 31
<211> LENGTH: 27
<212> TYPE: DNA
<213> ORGANISM: Artificial Sequence
<220> FEATURE:
<223> OTHER INFORMATION: TN10-forward primer

<400> SEQUENCE: 31
ggaggaagcg gccgcggtac tggcagt					27

<210> SEQ ID NO 32
<211> LENGTH: 26
<212> TYPE: DNA
<213> ORGANISM: Artificial Sequence
<220> FEATURE:
<223> OTHER INFORMATION: TN10-reverse primer

<400> SEQUENCE: 32
cctcctctct agagaggacc cggggc					26

<210> SEQ ID NO 33
<211> LENGTH: 27
<212> TYPE: DNA
<213> ORGANISM: Artificial Sequence
<220> FEATURE:
<223> OTHER INFORMATION: TN11-forward primer

<400> SEQUENCE: 33
ggaggaagcg gccgccgtcc tggtagc					27

<210> SEQ ID NO 34
<211> LENGTH: 26
<212> TYPE: DNA
<213> ORGANISM: Artificial Sequence
<220> FEATURE:
<223> OTHER INFORMATION: TN11-reverse primer

<400> SEQUENCE: 34
cctcctctct agagaggacg aggagc					26

<210> SEQ ID NO 35
<211> LENGTH: 27
<212> TYPE: DNA
<213> ORGANISM: Artificial Sequence
<220> FEATURE:
<223> OTHER INFORMATION: TN12-forward primer

```
<400> SEQUENCE: 35
ggaggaagcg gccgcggcac cggtgac                                              27

<210> SEQ ID NO 36
<211> LENGTH: 26
<212> TYPE: DNA
<213> ORGANISM: Artificial Sequence
<220> FEATURE:
<223> OTHER INFORMATION: TN12-reverse primer

<400> SEQUENCE: 36
cctcctctct agagagggcc aggatc                                               26

<210> SEQ ID NO 37
<211> LENGTH: 8
<212> TYPE: PRT
<213> ORGANISM: Artificial Sequence
<220> FEATURE:
<223> OTHER INFORMATION: An isolated polypeptide inhibiting binding
      between vascular endothelial cell growth factor receptor-2 and a
      vascular endothelial growth factor
<220> FEATURE:
<221> NAME/KEY: PEPTIDE
<222> LOCATION: (3)
<223> OTHER INFORMATION: an amino acid selected from the group
      consisting of Asn, Cys, Gln, Gly, Ser, Thr, Tyr, Asp, Glu, Arg,
      His, and Lys
<220> FEATURE:
<221> NAME/KEY: PEPTIDE
<222> LOCATION: (4)
<223> OTHER INFORMATION: an amino acid selected from the group
      consisting of Ala, Ile, Leu, Met, Phe, Pro, Trp, Val, Asp, Glu,
      Arg, His, and Lys

<400> SEQUENCE: 37

His Ile Xaa Xaa Gly Gln Trp Phe
  1               5
```